United States Patent [19]

Shaked et al.

[11] Patent Number: 4,530,787

[45] Date of Patent: Jul. 23, 1985

[54] CONTROLLED OXIDATION OF MICROBIALLY PRODUCED CYSTEINE-CONTAINING PROTEINS

[75] Inventors: Ze'ev Shaked, Berkeley; Sidney N. Wolfe, Richmond, both of Calif.

[73] Assignee: Cetus Corporation, Emeryville, Calif.

[21] Appl. No.: 661,902

[22] Filed: Oct. 17, 1984

Related U.S. Application Data

[63] Continuation-in-part of Ser. No. 594,351, Mar. 28, 1984, abandoned.

[51] Int. Cl.$^3$ .................... C07G 7/00; A61K 45/02
[52] U.S. Cl. .................... 260/112 R; 260/112.5 R; 424/85; 424/88; 435/68; 435/811
[58] Field of Search .................... 260/112.5 R, 112 R; 424/85, 88; 435/68, 811

[56] References Cited

U.S. PATENT DOCUMENTS

| | | | |
|---|---|---|---|
| 4,061,538 | 12/1977 | Dorner et al. | 260/112 R |
| 4,411,993 | 10/1983 | Gillis | 424/85 X |
| 4,414,147 | 11/1983 | Klibanov et al. | 260/112 R |
| 4,432,895 | 2/1984 | Tarnowski | 260/112 R |
| 4,450,103 | 5/1984 | Konrad | 260/112 R |
| 4,462,940 | 7/1984 | Hanisch et al. | 260/112 R |
| 4,478,744 | 10/1984 | Mezei et al. | 424/85 X |

OTHER PUBLICATIONS

Tietze, *Anal. Biochem.*, (1969), 27: 502–522.
Hellerman et al., *J. Am. Chem. Soc.*, (1941), 63: 2551–2553.
Chinard et al., *Methods Biochem. Anal.*, (1954), 1: 1–26.
Vallejos et al., *FEBS Letters*, (1976), 61: 95–99.
Guzman Barron, *Advan. Enzymol.*, (1951), 11: 223–226.
Liu, *The Proteins*, (1978), vol. III, 255–263, Academic Press.

*Primary Examiner*—Howard E. Schain
*Attorney, Agent, or Firm*—Albert P. Halluin; Janet E. Hasak

[57] ABSTRACT

Method of oxidizing reduced cysteine-containing microbially produced synthetic proteins, such as synthetic IFN-β or synthetic IL-2, in a controlled manner so that the synthetic proteins have the same disulfide bridging as their native counterparts. The oxidation employs o-iodosobenzoate as oxidizing agent and is carried out in an aqueous medium at a pH at least about one-half pH unit less than the $pK_a$ of the cysteines to be oxidized, a synthetic protein concentration of less than about 5 mg/ml, and an oxidizing agent:protein mol ratio that is at least stoichiometric, provided that the oxidizing agent is in excess in the terminal portion of the reaction.

22 Claims, No Drawings

CONTROLLED OXIDATION OF MICROBIALLY PRODUCED CYSTEINE-CONTAINING PROTEINS

This application is a continuation-in-part application of copending U.S. application Ser. No. 594,351 filed Mar. 28, 1984, now abandoned.

BACKGROUND OF THE INVENTION

1. Technical Field

This invention is in the field of biochemical engineering. More particularly, it concerns a method of oxidizing fully reduced cysteine-containing microbially produced proteins in a controlled manner so that they have disulfide bridging identical to their naturally occurring counterparts.

2. Background Art

When active proteins that contain one or more disulfide bridges are produced microbially via genetic engineering techniques, the synthetic protein is made by the microorganism in a reduced form lacking disulfide bridging or in the form of oligomers that are made in the cell by uncontrolled thiol-disulfide interchange reactions. Tietze, F., *Anal Biochem* (1969) 27:502. If it is desirable or necessary that the synthetic protein have the same primary structure as its native counterpart, the biochemical engineer is faced not only with the problem of separating the protein from the microorganism culture, but also the problems of reducing oligomers and/or oxidizing the reduced synthetic protein so that it assumes the primary structure of the native protein. Previous oxidations of synthetic microbially produced proteins have been uncontrolled and done deliberately by subjecting the protein to oxidizing conditions or incidentally by placing the proteins in an environment in which it is oxidized. Oxidizing the protein in an uncontrolled manner may: result in the formation of undesirable isomers (incorrect intramolecular bridging) or polymers (intermolecular bridging); overoxidation; complicate the separation of the protein from the culture, or reduce the yield of protein having the desired primary structure. In the case of proteins that are intended for therapeutic use, uncontrolled oxidation through purification, formulation or administration yields a nonhomogeneous material that is contaminated with isomers and/or oligomers that may be inactive or antigenic.

The present invention is directed to a process for oxidizing such microbially produced proteins in a selective, controlled manner using an oxidizing agent, preferably o-iodosobenzoic acid, that oxidizes cysteines selectively, such that the desired disulfide bridging is produced in high yield. In this regard, o-iodosobenzoic acid is a well known sulfhydryl reagent that has been used previously to oxidize vicinal cysteines of native proteins selectively. Hellerman, L., et al., *J Amer Chem Soc* (1941) 63:2551-2552, Chinard, F. P. and Hellerman, L., *Methods Biochem Anal* (1954) 1:1, and Vallejos, R. H. and Andreo, C. S., *FEBS* Letters (1976) 61:95-99. Other oxidizing agents for thiol groups in native proteins are described by Guzman Barron, E. S., *Advan Enzymol* (1951) 11:223-226 and Teh-Yung Liu, *The Proteins* (1978) Vol III, 255-263, Academic Press, N.Y. To the best of applicants' knowledge, prior use of o-iodosobenzoic acid and other oxidizing agents as selective oxidants for sulfhydryl groups in proteins has been for analytical purposes. Applicants know of no prior art concerning the use of such oxidants in preparative processes to carry out controlled oxidation of synthetic microbially produced proteins.

SUMMARY OF THE INVENTION

The invention is a preparative process for oxidizing a fully reduced microbially produced synthetic protein having an amino acid sequence substantially identical to a useful protein which sequence includes cysteines which in the useful protein are linked intramolecularly to form a cystine in a controlled manner whereby said cysteines are oxidized selectively to form said cystine with minimal overoxidation and formation of nonconforming cysteine groups or oligomers comprising reacting the fully reduced microbially produced synthetic protein with an o-iodosobenzoate in an aqueous medium at a pH at least about one-half pH unit lower than the $pK_a$ of said cysteines and wherein the concentration of synthetic protein in the reaction mixture is less than about 5 mg/ml and the mol ratio of o-iodosobenzoate to protein is at least stoichiometric, with the proviso that the o-iodosobenzoate is in excess in the terminal portion of the reaction.

Also part of this invention are novel oxidized preparations produced by the above-described controlled oxidation of synthetic proteins having an amino acid sequence substantially identical to a useful protein which sequence includes cysteines which in the useful protein are linked intramolecularly to form a cystine. Preferably the protein is a mutein as defined further below or microbially produced IFN-$\beta$ or IL-2. These preparations comprise a synthetic protein that (a) has the same disulfide bridging as its native counterpart, (b) is substantially free of oligomers and (3) contains less than about 15% of isomers having disulfide bridging different from its native counterpart.

DESCRIPTION OF THE PREFERRED EMBODIMENTS

The synthetic proteins that are oxidized by the invention are exogenous to the genetically engineered microorganisms that produce them. They have amino acid sequences that are substantially identical to useful proteins and include cysteine residues which in the useful protein are linked intramolecularly to form one or more cystine (intrapeptidal disulfide bridges) moieties. In this regard the term "substantially identical" means that the amino acid sequences of the synthetic and useful proteins are either identical or differ by one or more amino acid alterations (deletions, additions, substitutions) that do not cause an adverse functional dissimilarity between the synthetic protein and its nonmicrobially produced counterpart. The synthetic proteins that are oxidized in the invention process are fully reduced, i.e., they lack disulfide bridging. If the protein is produced by the microorganism in an oxidized form it must be reduced before being subjected to the oxidation. Reduction may be accomplished by treating the protein with a reducing agent such as dithiothreitol or 2-mercaptoethanol.

Synthetic proteins of particular interest are those that have amino acid sequences that are substantially identical to native proteins having useful biological activity and disulfide bridging that is essential to such activity or enhances such activity. Examples of such native proteins are lymphokines such as interferon-beta (IFN-$\beta$), the interferon-alphas (IFN-$\alpha$), interleukin-2 (IL-2), and colony stimulating factor-1.

Also of particular interest are synthetic proteins which are muteins of biologically active proteins in which at least one cysteine residue that is not essential to biological activity, that is present in the biologically active protein and that is free to form a disulfide link has been deliberately deleted or replaced with another amino acid to eliminate sites for intermolecular crosslinking or incorrect intramolecular disulfide bond formation.

Proteins which may be mutationally altered in this manner may be identified from available information regarding the cysteine content of biologically active proteins and the roles played by the cysteine residues with respect to activity and tertiary structure. For proteins for which such information is not available in the literature, this information may be determined by systematically altering each of the cysteine residues of the protein by the procedures described herein and testing the biological activity of the resulting muteins and their proclivity to form undesirable intermolecular or intramolecular disulfide bonds. Accordingly, while the invention is specifically exemplified below as regards muteins of IFN-β and IL-2, it will be appreciated that the following teachings apply to any other biologically active protein that contains a functionally nonessential cysteine residue that makes the protein susceptible to undesirable disulfide bond formation. Examples of proteins other than IFN-β and IL-2 that are candidates for mutational alteration according to the invention are lymphotoxin (tumor necrosis factor), colony stimulating factor-1, and IFN-α1. Candidate proteins will usually have an odd number of cysteine residues.

In the case of IFN-β it has been reported in the literature that both the glycosylated and unglycosylated IFNs show qualitatively similar specific activities and that, therefore, the glycosyl moieties are not involved in and do not contribute to the biological activity of IFN-β. However, bacterially produced IFN-β which is unglycosylated consistently exhibits quantitatively lower specific activity than native IFN-β which is glycosylated. IFN-β is known to have three cysteine residues at positions 17, 31 and 141. Cysteine 141 has been demonstrated by Shepard, et al., supra, to be essential for biological activity. In IFN-α, which contains four cysteine residues, there are two intramolecular —S—S— bonds: one between cys 29 and cys 138 and another between cys 1 and cys 98. Based on the homology between IFN-β and IFN-αs cys 141 of IFN-β could be involved in an intramolecular —S—S— bond with cys 31, leaving cys 17 free to form intermolecular crosslinks. By either deleting cys 17 or substituting it by a different amino acid, one can determine whether cys 17 is essential to biological activity, and its role in —SS— bond formation. If cys 17 is not essential for the biological activity of the protein, the resulting cys 17-deleted or cys 17-substituted protein might exhibit specific activity close to that of native IFN-β and would possibly also facilitate isolation and purification of the protein.

By the use of the oligonucleotide-directed mutagenesis procedure with a synthetic oligonucleotide primer that is complementary to the region of the IFN-β gene at the codon for cys 17 but which contains single or multiple base changes in that codon, a designer gene may be produced that results in cys 17 being replaced with any other amino acid of choice. When deletion is desired the oligonucleotide primer lacks the codon for cys 17. Conversion of cys 17 to neutral amino acids such as glycine, valine, alanine, leucine, isoleucine, tyrosine, phenylalanine, histidine, tryptophan, serine, threonine and methionine is the preferred approach. Serine and threonine are the most preferred replacements because of their chemical analogy to cysteine. When the cysteine is deleted, the mature mutein is one amino acid shorter than the native parent protein or the microbially produced IFN-β.

Human IL-2 is reported to have three cysteine residues located at positions 58, 105, and 125 of the protein. As in the case of IFN-β, IL-2 is in an aggregated oligomeric form when isolated from bacterial cells and has to be reduced with reducing agents in order to obtain a good yield from bacterial extracts. In addition, the purified reduced IL-2 protein is unstable and readily reoxidized upon storage to an oligomeric inactive form. The presence of three cysteines means that upon reoxidation, the protein may randomly form one of three possible intramolecular disulfide bridges, with only one of those being the correct bridge as found in the native molecule. Since the disulfide structure of the native IL-2 protein is not known, it is possible to use the present invention to create mutations at codons 58, 105 and 125 of the IL-2 gene and identify which cysteine residues are necessary for activity and therefore most likely to be involved in native disulfide bridge formation. In the same vein, the cysteine residue that is not necessary or activity can be modified so as to prevent the formation of incorrect intramolecular disulfide bridges and minimize the chance of intermolecular disulfide bridges by removal or replacement of the free cysteine residue.

The synthetic counterparts, including the above-described muteins, of the native proteins which may be oxidized are made by genetic engineering techniques. These techniques typically involve identifying and characterizing the structural gene that encodes the native protein, isolating or synthesizing that gene or a mutant that encodes a functionally equivalent mutein of the native protein, inserting the gene into an appropriate expression vector in a position that permits expression of the gene, transforming competent microorganisms with the vector, identifying correct transformants, and culturing the transformants in a suitable growth medium. The protein is typically recovered from the culture by disrupting the cells, treating the disruptate with solubilizing agents (depending on the solubility characteristics of the protein) and one or more extractants to isolate crude protein, and purifying the crude protein by various preparative chromatography procedures. If the protein is produced by the microorganisms in oligomeric form or is susceptible to oligomer formation during the recovery, the protein will be treated with a reducing agent at an appropriate stage in the recovery process.

After the synthetic protein is recovered from the microorganism in a crude, substantially pure, or pure form, it is reduced, if necessary, and then oxidized in a controlled manner using the invention process. Controlled oxidation pursuant to the invention process causes the formation of disulfide bridging in the synthetic protein that conforms to the bridging in its native counterpart with no or minimal overoxidation and formation of nonconforming bridging or oligomers. Such oxidation enables the production of high yields of the synthetic protein in a configuration that most closely resembles the configuration of its native counterpart, thereby ensuring the likelihood that the synthetic protein will be functionally equivalent to the native protein.

The oxidant (o-iodosobenzoate) that is used in the process oxidizes cysteine residues selectively and stoichiometrically. In this regard, the term "selectively" indicates that the oxidant (1) oxidizes the cysteines to the disulfide level with no or insignificant oxidation to higher levels and (2) preferentially oxidizes active cysteines that are positioned proximately in the reduced protein. The mol ratio of oxidant to synthetic protein may vary widely depending on the oxidant used. The mol ratio will be at least stoichiometric (1:1 or greater) and will typically be in the range of 1:1 to 100:1. In the case of o-iodosobenzoate, the mol ratio will usually be in the range of about 1:1 to about 5:1. In all instances, the oxidant is in excess during the terminal portion of the reaction to ensure complete oxidation of the reduced protein. These conditions may be achieved by running the reaction with excess oxidant over its entire duration or running the reaction with approximately equimolar portions of reactants over the majority of the reaction period and adding excess oxidant near the end of the reaction period. If the protein is particularly susceptible to oligomerization it is preferable to use reactant proportions that effect pseudo first order kinetics for the oxidant. Such kinetics occur when the oxidant is present in slight excess within the above-mentioned mol ratio range. The concentration of protein in the reaction mixture is kept low, i.e., less than about 5 mg/ml, usually about 0.1 to about 1.5 mg/ml, and preferably about 0.3 to about 0.7 mg/ml, in order to reduce the likelihood of oligomer formation.

The pH of the reaction medium is maintained at a level at least about one-half pH unit below the $pK_a$ of the cysteine residues being oxidized. When the $pK_a$s of these residues differ, the pH is preferably maintained at least about one-half pH unit less than the cysteine residue having the lowest $pK_a$. Control of the pH in this manner controls the amount of nonionized thiol, thereby controlling the rate of the reaction and favoring the formation of the desired disulfide bridging. Use of pHs significantly above the specified pH may cause increased production of undesired isomers and oligomers. Excessively high pHs, i.e., greater than about 9, may result in increased oligomer formation and are, therefore, not recommended in most instances. For synthetic IFN-$\beta$ the pH is maintained between 6 and 9, preferably 6.5 and 8.0. For synthetic IL-2, it is maintained between 5.5 and 9, preferably 7.0 and 8.0.

Thiol $pK_a$ values may be determined by the procedures described by Irving, R. J., et al., *Acta Chemica Scandinavica* (1964) 18:769-787; Shaked, Z., et al, *Biochemistry* (1981) 19:4256-4266; and Snyder, G. H., et al., *Biochemistry* (1981) 20:6509-6519 and the desired pH range for a given synthetic polypeptide calculated from such determinations. Alternatively, operable and preferred pH ranges for oxidizing a given synthetic protein may be determined empirically.

The oxidation reaction time will depend upon the volume of the reaction mixture. The reaction temperature is not critical and will normally be between 20° C. and 25° C., conveniently room temperature. The oxidation reaction may be terminated by lowering the pH to a level at which the reaction ceases (about pH 4.5). Following the reaction, residual oxidizing agent and undesired isomers and oligomers may be removed chromatographically. If necessary, the oxidized protein may be purified further using protein purification procedures such as gel filtration, high performance liquid chromatography, followed by diafiltration or the like.

In one preferred purification technique for the oxidized protein, small molecular weight species such as sodium dodecyl sulfate or the o-iodosobenzoic acid are removed from the protein pool using gel filtration, for example, a Sephadex G-25 desalting column, rather than diafiltration. Such a gel filtration process generally represents a simple, rapid, reliable, mild, high-recovery process for the purification. For purifying interferon-beta and IL-2 the G-25 desalting column step may be used to remove the solubilizing detergent SDS which is present during oxidation. For IFN-$\beta$ an alkaline environment of 10 mM sodium hydroxide is generally required due to the insolubility of the interferon-beta in neutral solutions of pH 6-8. With diafiltration the interferon is subjected to an alkaline pH 12 environment for as long as 4-5 hours so that heterogenicity is introduced into the sample. Gel filtration reduces the total incubation time at pH 12 to only 20-70 minutes depending on the flow rate. In addition, it is possible to run the G-25 desalting column at lower pH values of 10.3-11. These two improvements eliminate heterogenicity which has been observed in the post-diafiltered interferon-beta. The only disadvantage of using gel filtration, dilution of the protein, can be controlled by optimizing the sample loading and by choosing the smallest grade of particle size. Furthermore, in most processes gel filtration is not the final step so that concentration or a further dilution of the sample occurs.

The preparation produced by the controlled oxidation consists essentially of synthetic protein having the disulfide bridging of its native counterpart. It is substantially free of oligomers (less than about 1% by weight) and contains less than about 15% by weight isomers having disulfide bridging different from the native counterpart. Synthetic proteins that have been designed to eliminate the possibility of isomer formation (e.g., IL-2 in which the cysteine at position 125 has been changed to serine or IFN-$\beta$ in which the cysteine at position 17 has been changed to serine), of course, contain no isomers. In contrast, preparations made via uncontrolled oxidations typically contain significant amounts of oligomers (5%-10%) and much larger amounts of undesired isomers. In the case of IL-2 and IFN-$\beta$, the oxidized proteins are more water soluble than the reduced species. Accordingly, the solubilizing agent (e.g., SDS) may be substantially removed from the preparation, leaving a purified product that is sufficiently water soluble to permit formulation with conventional aqueous parenteral vehicles.

Since the preparations prepared by the controlled oxidization contain more desired product and fewer contaminants than preparations made via uncontrolled oxidation, they may be less antigenic and will usually be more active. Preparations of therapeutic proteins will comprise a therapeutically effective amount of the protein in admixture with a pharmaceutically acceptable carrier. In the case of IFN-$\beta$ and IL-2, the preparation will usually be formulated for parenteral administration in aqueous vehicles such as distilled water, Ringer's solution, Hank's solution, and physiological saline. IFN-$\beta$ will usually be administered to humans at doses in the range of $1 \times 10^5$ to $4 \times 10^8$ units, whereas IL-2 will usually be administered at about $1 \times 10^4$ to $2 \times 10^8$ units.

The following examples further illustrate the invention process. These examples are not intended to limit the invention in any manner. In these examples all temperatures are in degrees Celsius unless otherwise indicated.

EXAMPLE 1

Controlled Oxidation of IFN-$\beta_{ser17}$

Preparation of Fully-Reduced IFN-$\beta_{ser17}$

IFN-$\beta_{ser17}$ is a microbially produced mutein of IFN-$\beta$ in which the cysteine residue at amino acid position 17 is replaced with a serine residue. IFN-$\beta_{ser17}$ has two remaining cysteine residues: one at position 31 and the other at position 141. In native IFN-$\beta$ the cysteines at positions 31 and 141 interact to form a disulfide bridge. The genetically engineered E. coli microorganism strain used in this example to produce IFN-$\beta_{ser17}$ was deposited in the American Type Culture Collection, 12301 Parklawn Drive, Rockville, Md. 20852 USA on Nov. 18, 1983 under accession number 39,517.

These genetically engineered E. coli were grown in the following medium:

| Ingredient | Approximate Initial Concentration |
| --- | --- |
| Na$_3$ Citrate.2H$_2$O | 3 mM |
| KH$_2$PO$_4$ | 30 mM |
| (NH$_4$)$_2$SO$_4$ | 74 mM |
| MgSO$_4$.7H$_2$O | 3 mM |
| MnSO$_4$.H$_2$O | 46 $\mu$M |
| ZnSO$_4$.7H$_2$O | 46 $\mu$M |
| CuSO$_4$.5H$_2$O | 1–2 $\mu$M |
| L-tryptophan | 350 $\mu$M |
| FeSO$_4$.7H$_2$O | 74 $\mu$M |
| thiamine.HCl | 0.002% |
| glucose | 0.5% |

Dow Corning Antifoam B, 25% solution, glucose, 50% solution, and KOH, 5N, were added on demand.

Temperature was maintained at 37 ±1° C., pH at 6.5±0.1 with NaOH, and dissolved oxygen at 30% of air saturation. Optical density and residual glucose measurements were taken at 14 hours and at approximately one hour intervals thereafter. Harvest was made when glucose consumption reached 40±6 g/l (OD at 680 nM=10–11).

The harvested material was concentrated approximately 3-fold by circulating it through a microporous cross-flow filter under pressure. The concentrated cells were diafiltered against deionized water until the harvest material was concentrated 4–5 fold. The cells were then disrupted by passing them through a Manton-Gaulin homogenizer at 4.1–5.5×10$^4$ kpa. After the initial pass sodium dodecyl sulfate (SDS)-sodium phosphate buffer was added to a final concentration of 2% SDS, 0.08M sodium phosphate, and homogenization was continued for one hour. Solid dithiothreitol (DTT) was then added to a final concentration of 50 mM and the homogenizate was heated to 90±5° C. for 10 minutes. The resulting cell suspension was extracted with 2-butanol at a 1:1 2-butanol:suspension volume ratio in a static mixer. The mixture was then centrifuged and the 2-butanol rich phase was collected.

The 2-butanol rich phase was mixed with 2.5 volumes of 0.1% SDS in phosphate buffered saline (PBS). Solid DTT was added to a final concentration of 1 mM. The pH of the mixture was adjusted to 6.2±0.1 with glacial acetic acid and this mixture was centrifuged. The resulting paste was collected and resuspended in PBS +10% SDS with pH adjustment to 8.5±0.1 using 1N NaOH. Solid DTT was added to a final concentration of 100 mM and the suspension was heated to 90±5° C. for 10 minutes. The suspension was then cooled to about 25° C., the pH was adjusted to 5.5±0.1 with glacial acetic acid, and the solution was filtered.

The solution was then applied to a Sephacryl S-200 precolumn and the fractions containing highest interferon activities were pooled and concentrated by ultrafiltration with a 10 Kdal molecular weight cut-off.

Oxidation of Fully Reduced IFN-$\beta_{ser17}$

A 1 mM o-iodosobenzoic acid solution was prepared by mixing the acid in water, sonicating the mixture for about 5 minutes and then stirring and adding 2% NaOH slowly to obtain a final pH of 8.2±0.2 (additional sonication may be used as an alternative to adding base).

A reaction buffer medium was prepared by dissolving Na$_4$P$_2$O$_7$.10H$_2$O in water to a concentration of 2 mM. The pH of this solution was adjusted to 9.0 by adding 10% acetic acid. SDS to 0.1%, ethylenediaminetetraacetic acid (EDTA) to 1mM and the o-iodosobenzoic acid solution to 15×10$^{-6}$M were added to the solution.

The buffer medium was placed in a reaction vessel equipped with a magnetic stirrer and a pH electrode set at 9.0. The IFN-$\beta_{ser17}$ preparation and the o-iodosobenzoic acid solutions were added to the reaction mixture from holding vessels using peristaltic pumps that were calibrated to introduce equivalent mol ratios of the IFN and oxidizing agent. The pH of the reaction mixture was controlled at 9.0 by adding 0.25M NaOH via a peristaltic pump at 5 ml/hr. as needed. The IFN-$\beta$ solution (5 mg/ml in 50 mM acetate buffer, pH 5.5) was added at a flow rate of 2 ml/hr. (7.0 micromole/hr.) for about 5 hours; the o-iodosobenzoic acid solution was added at 7 ml/hr. (7 micromole/hr.) over the same time period. The addition of the acid solution was continued thereafter to get a final excess of 10–15 mol. The reaction was followed by reverse phase HPLC and by assaying the residual thiol content of IFN-$\beta_{ser17}$ by Ellman's assay. After 6.5 hours the reaction was terminated by adding 10% acetic acid to the reaction mixture to a pH of 5.5.

Results

During the first 2–3 hours of the reaction, no oligomers or only low levels (<1%) of oligomers were formed. The level of oligomeric species decreased substantially during the later stages of the reaction. The oxidized product contained no free thiols and the desired oxidized product was obtained in yields exceeding 96%.

In comparison, an IFN-$\beta_{ser17}$ oxidation was carried out in which o-iodosobenzoic acid (2 mg/ml) was added to the reaction mixture at once to a concentration of 5 mmol. This oxidation resulted in the formation of 10%–15% oligomers and only moderate recovery (80%) of the desired oxidized IFN was obtained.

EXAMPLE 2

Controlled Oxidation and Purification of IFN-$\beta_{ser17}$

1. Controlled Oxidation of Fully Reduced IFN-$\beta_{ser17}$

The procedure described in Example 1 was used to prepare a solution of IFN-$\beta_{ser17}$ in the fully reduced form except for the final pre-column step. A total of 1–2 mg/ml of the solution in DTT was run on a S-200 column and eluted with a sodium acetate buffer (50 mM, pH 5.5, 0.1% SDS). The S-200 IFN-$\beta$ pool was diluted to 0.1 mg/ml (5 micromolar IFN-$\beta$) by adding sodium phosphate buffer, pH 7.5, 0.1% SDS. The pH of the solution was adjusted to 7.5. The oxidizing reagent iodosobenzoic acid (2 mg/ml) was added to the IFN-β solution in order to obtain a final concentration of 40 micromolar. This IFN-oxidant solution was kept for 3 hours at room temperature under air and was gently stirred. The oxidation was followed by monitoring the thiol content of the protein solution using 2,2'-dithiodipyridine. The IFN-β was concentrated to 5-10 mg/ml by using an Amicon cell and then run through a G-75 column using the same buffer that was used for the S-200 column. The final IFN-β concentration was 2-3 mg/ml.

2. Gel Filtration of the G-75 IFN-β Pool by a G-25 Sephadex Column

A 2.6×70 cm glass column (Pharmacia) equipped with a packing reservoir was packed with 600 ml of pre-swelled gel solution of Sephadex G-25 (fine grade).

A total of 10 ml (1.44 mg/ml) of IFN-β from the previous step was introduced to the column and eluted by using a 1 mM NaOH solution at pH 10.8. A flow rate of 250 ml/hr. was employed. Approximately 98% of the protein peak was pooled together and analyzed for protein concentration, SDS and biological activity. In addition, reverse phase HPLC and SDS-PAGE gels were obtained.

3. Reverse Phase HPLC Method

The protein sample that was collected from the column was acidified to pH 2-3 by adding concentrated tri-fluoro acetic acid (TFA). The HPLC traces were obtained by injecting 20-200 microliters to an Aquapore column. The elution of the sample was followed at 214 nm and performed by using a two-solvent system and a gradient of 45-60% solvent B where solvent B is 0.1% TFA in acetonitrile and solvent A is 0.1% TFA in water. A flow rate of 2 ml/min. and a chart speed of 0.5 cm/min. were used. An Hewlett-Packard integrator was used to obtain the areas of the peaks.

4. SDS Determinations

The SDS determinations were done by the acridine orange assay by placing an IFN-β sample (0.5 ml) in a disposable 13×100 mm screw cap test tube followed by $NaHSO_4$ (0.1 ml, 1.75M), acridine orange (0.1 ml, 1% wt/v) and finally toluene (1.5 ml). The test tubes were sealed and then vortexed for 2-3 minutes. The tubes were centrifuged for 5-10 minutes. After phase separation the organic layer was transferred to a quartz cuvette and the absorbance was measured at 500 nm versus a blank (0.5 ml of water).

5. Formulation of IFN-β with Normal Serum Albumin (NSA)

The formulation of IFN-β with NSA was done by first calculating the final volume factor (F.V.) to obtain the NSA, dextrose and water volumes which were needed for the formulation.

The Final Volume=IFN-β/0.25
The NSA Volume=1.25/25×F.V.
The Dextrose Volume=1.25/50×F.V.
The H₂O Volume=F.V.-[V(IFN-β)+V(HSA)+V-(Dext)+V(neut)]

By a typical procedure (NSA, 3.9 ml, 25% solution obtained from Travenol) was mixed with 46 ml water. The pH was raised to 12 by employing a NaOH (2.5N) solution and monitoring it using an electrode. The IFN-β solution (20 ml) was added and the mixture was held at pH 12 for 15 minutes. The pH was slowly lowered to 7.23 by using a HCl (2.5N or 0.25N) solution. The pH adjustment required about 10-15 minutes. Water (2 ml) and dextrose (1.9 ml, 50%) were added. The final IFN-β concentration was 0.25 mg/ml. The final formulated solution was filtered through 0.2 microns Nalge sterilized filter and the filtered solution was used to fill the vials (1 ml in each vial). The vials were lyophilized and then capped. Upon lowering the pH to 7.3 the solution did not produce a haze and remained clear.

6. Biological Activities

Biological activities were determined by using the yield reduction assay, which is the direct measurement of virus yields from IFN-treated cells. The assay protocol followed that of Stewart and Lockhart described in *Journal of Virology*, 6, 795-799 (1970).

7. Results

The SDS-PAGE gel and the reverse phase HPLC trace indicate that the oxidized IFN-β preparation was homogeneous and basically pure. Two runs on the oxidized material, summarized in Table I, indicate that the gel filtration G-25 column was effective in desalting the pool of oxidized IFN-β to acceptable levels of SDS as determined by the acridine orange assay described by *Anal. Biochem.*, Vol. 118, p. 138-141 (1981) with minor modifications of volumes and pH levels. The total time in the column can be as short as 30 minutes without affecting the efficiency of SDS removal. The DTT levels in the G-25 pool was hardly detectable. The recovery of IFN-β from the column was essentially quantitative and the dilution factor was less than two. Reverse phase HPLC traces indicate that the incubation of the oxidized form of IFN-β in 1 mM NaOH at pH 10.8 did not introduce heterogenicity in the IFN-β preparation, at least as determined by the HPLC method. The HPLC traces also indicate that the NSA-formulated and filtered IFN-β HPLC trace did not change even after five days.

The SDS-PAGE reducing gel of the G-25 desalted protein also indicates that a single protein population was obtained.

The biological activity of the protein remained essentially the same during all the stages of the modified process, indicating that the oxidized IFN-β remained essentially unchanged during the gel filtration stage.

TABLE I

| Parameters and Assay Results | Run #1 | Run #2 |
|---|---|---|
| Buffer | 1 mM NaOH | 1 mM NaOH |
| pH | 10.8 | 10.8 |
| Volume of IFN-β solution (ml) | 10 | 10 |
| IFN-β concentration (mg/ml) | 1 | 1.44 |
| Volume of G-25 pool (ml) | 28 | 30 |
| IFN-β concentration after desalting (mg/ml) | 0.36 | 0.48 |
| Recovery (%) | 99 | 99 |
| Flow rate (ml/hr.) | 300 | 250 |
| Total time in the column (min.) | 32 | 37 |
| SDS level (microgram/mg) | 21 | 21 |
| Biological activity (U/mg) | $9.1 \times 10^7$ | $9.2 \times 10^7$ |

EXAMPLE 3

Oxidation of Fully Reduced IL-2

Preparation of Fully Reduced IL-2

IL-2 was recovered from *E. coli* K-12 strain MM294 that had been transformed with the plasmid pLW1 (deposited at the American Type Culture Collection on Aug. 4, 1983 under ATCC Number 39,405) as follows.

The genetically engineered *E. coli* were grown in a fermenter using the following growth medium.

| | |
|---|---|
| $(NH_4)_2SO_4$ | 72 mM |
| $KH_2PO_4$ | 21.6 mM |
| $Na_3$ Citrate | 1.5 mM |
| $ZnSO_4.7H_2O$ | 60 mM |
| $MnSO_4.H_2O$ | 60 mM |
| $CuSO_4.5H_2O$ | 2 mM |
| pH adjusted to 6.50 with 2.5 N NaOH autoclaved | |
| Sterile Additions (post autoclave) | |
| $MgSO_4.7H_2O$ | 3 mM |
| $FeSO_4$ | 100 μM |
| L-tryptophan | 70 mg/l |
| Thiamine-HCl | 20 mg/l |
| Glucose | 5 g/l |
| Tetracycline | 5 mg/l |
| Ethanol (optional) | 2% |
| Casamino acid | 2% |

Dow Corning Antifoam B, 20% solution, glucose, 50% solution, and KOH, 5N, were added on demand.

The pH of the fermenter was maintained at 6.8 with 5N KOH. Residual glucose was maintained between 5-10 g/l, dissolved oxygen at 40%, and temperature at 37°±1° C. The casamino acids (20% stock solution) were added when the $OD_{680}$ was about 10-15. Harvest was made two hours after ethanol addition. Three hours after adding the casamino concentrated solution, ethanol (95%) was added to get a final 2% concentration.

Cells were concentrated in a cross-flow ultrafiltration unit. The cells were washed and then disrupted in a Manton-Gaulin homogenizer. The cell disruptate was centrifuged. The paste was resuspended in 4M urea and let stand for 15-30 minutes. The urea washed fragments were centrifuged and resuspended in Tris-HCl buffer, pH 8.0. Solid SDS was added to a level of 5% SDS in order to solubilize the fragments.

The urea washed solution (200 ml) was reduced by DTT (10 mM) in the presence of EDTA (2.5 mM) at pH 8.0 and 60° C. for 30 minutes. The suspension was centrifuged at 35K for two hours. The supernatant (35 ml) was loaded on a S-200 (K-50) column and eluted with buffer E (acetate pH 5.5, DTT (2 mM), EDTA (1 mM) and SDS (0.1%)) at a rate of 1.5 ml/min. The S-200 pool (270 ml, $A_{280}$=1.77) was about 33% pure as determined by HPLC.

A portion of the S-200 pool (35 ml) was acidified with trifluoroacetic acid (TFA) to pH 2.0, and then loaded at 2.5 ml/min. on a semi-preparative (1.3 cm) C-4 Vydac column that was freshly prepared. This was done three times with 35 ml each loading. The solvent used for this semi-preparative purification was acetonitrile (0.1% TFA, buffer B) and the gradient that was used was 0% to 45% buffer B in 15 minutes followed by 45% to 75% of B in 200 minutes. The IL-2 pool came out as 76 ml (three runs) with an $A_{280}$=0.326 that corresponds to about 25 mg of IL-2 and which is about 15% yield. This HPLC run was diluted into 1600 ml of $Na_2PO_4$ buffer (0.1M, pH 7.0, 0.1% SDS) and then concentrated to 50 ml by using an Amicon cell equipped with a 76 mm PM-10 membrane. The concentrate was washed with three volumes of 50 ml each of $Na_2PO_4$ (50 mM) pH 7 buffer which contained 0.1% SDS. The final volume was 43 ml with an $A_{280}$=0.65.

Controlled Oxidation of IL-2

Before the controlled oxidation was carried out, the total thiol content of the protein solution was determined with 2,2'-dithiodipyridine. This determination was necessary in order to calculate the minimum theoretical amount of o-iodosobenzoic acid that had to be added to the IL-2 solution to achieve complete oxidation. o-Iodosobenzoic acid solution (1 mM, 50 ml) was prepared by dissolving the compound (13.4 mg) in about 45 ml of $H_2O$ by sonicating the mixture for a few minutes and then by stirring the slowly adding NaOH (1N) to dissolve the acid. The alkaline solution was added to obtain a final pH of 8.0 to 8.5. The volume of the oxidant solution was adjusted to a final volume of 50 ml. A sulfhydryl group determination was done in order to determine the total amount of oxidant needed for a complete oxidation. This corresponded to the total thiol concentration divided by two plus a 15 micromolar excess of the oxidant. The controlled oxidation was performed by adding the o-iodosobenzoic acid solution at a flow rate of 0.5 ml/hr. to the IL-2 solution (50 mM $Na_2PO_4$, pH 7 or 7.5). The degree of the oxidation was monitored by reverse phase HPLC. The oxidation was stopped by lowering the pH of the solution to 5.5 using concentrated acetic acid. HPLC analysis of the oxidized product showed that it comprised about 80% of the desired oxidized IL-2, about 13% undesired isomers (the isomers were collected, assayed for IL-2 activity and found to be inactive) and about 6% reduced (unoxidized) IL-2.

A similar oxidation carried out at ph 7.5 provided significantly reduced conversion (54%) to the desired product.

Purification of Oxidized IL-2

The oxidized product was purified essentially by the same method that was described for the purification of reduced IL-2. Two loadings (20 ml each) were performed on the 1.3 cm column. The pooling of this HPLC run was determined by analyzing the individual fractions on an analytical reverse phase HPLC column. The total volume of the two HPLC runs corresponds to 18 ml with an $A_{280}$=0.266, which is about 4.8 mg of oxidized and HPLC purified IL-2.

The organic solvent was removed by using a Speed-Vac. After completely drying the test tube from the organic solvent, sodium phosphate buffer (0.1M, pH 7.0) was added, followed by 0.1 ml SDS (1%) and sonication to ensure complete solubility. The total volume (3 ml) was loaded on a G-25 (medium) column (1.5×23 cm) and eluted with a sodium phosphate buffer (2 mM, pH 7.5) with a flow rate of 45 ml/hr. The final volume that was obtained was 5.1 ml and 0.6 mg of IL-2 per ml. The protein concentration was determined by the Lowry method. An assay of the total content of alkyl sulphates was performed by the acridine orange method. The total alkyl sulphate residual content was about 42 micrograms per mg of IL-2.

Storage stability tests of this purified oxidized IL-2 at pH 7.5 at 5° C. and room temperature indicated the material is stable (i.e., IL-2 activity remains unchanged) over prolonged time periods.

EXAMPLE 4

Oxidation of Fully-Reduced Des-AlaIL-2$_{ser125}$

Des-ala IL-2$_{ser125}$ is an IL-2 whose amino acid sequence differs from native human IL-2 by the absence of the initial N-terminal alanine residue and a serine substituted for cysteine at position 125. The strain of des-ala IL-2$_{ser125}$-producing *E. coli* used for this example was deposited in the ATCC on Mar. 6, 1984 under accession number 39,626.

These genetically engineered des-ala IL-2$_{ser125}$-producing *E. coli* were grown, the cells disrupted, and the cellular debris was recovered from the disruptate using the general procedures of Example 2. The cellular debris was extracted with 4M urea as in Example 2. The resulting paste was resuspended in aqueous buffer and solubilized with SDS. DTT, 150 mM, was added to the solution and the IL-2 was reduced by heating to 40° C. at pH 8.5. The mixture was cooled and its pH adjusted to 5.0. The solution was then extracted with 2-butanol (1:1 v/v ratio) containing 1 mM DTT at room temperature. The organic extract was chromatographed on a S-200 column (as in Example 2) and then on a G-25 column using buffer E.

The G-25 pool was oxidized using the general procedure of Example 2. Following the oxidation, the oxidized product was purified by RP-HPLC using a Vydac TP214 packing and a solvent system of propanol in 1M acetic acid (gradient 35%–60% propanol over 200 min.). The recovered IL-2 was then diluted in 50 mM acetate buffer. pH 5.5, 6 mM EDTA, 0.1% SDS, and SDS was removed by G-25 column gel filtration using a 2 mM sodium phosphate, pH 7.5 buffer. The resulting oxidized, purified product is suitable for formulation for parenteral administration. The formulated composition may be lyophilized for storage.

Modification of the above-described modes for carrying out the invention that are obvious to those of skill in biochemical engineering are intended to be within the scope of the following claims.

What is claimed is:

1. A preparative process for oxidizing a microbially produced synthetic protein having fully reduced cysteines and having an amino acid sequence substantially identical to a useful protein which sequence includes cysteines which in the useful protein are linked intramolecularly to form a cystine in a controlled manner whereby said cysteines are oxidized selectively to form said cystine with minimal overoxidation and formation of nonconforming cysteine groups or oligomers comprising reacting the fully reduced microbially produced synthetic protein with o-iodosobenzoate in an aqueous medium at a pH at least about one-half pH unit below the pK$_a$ of said cysteines and wherein the concentration of synthetic protein in the reaction mixture is less than about 5 mg/ml and the mol ratio of o-iodosobenzoate to protein is at least stoichiometric, with the proviso that the o-iodosobenzoate is in excess in the terminal portion of the reaction.

2. The process of claim 1 wherein the useful protein is a native protein having useful biological activity and the intramolecular linking is essential to the biological activity or enhances the biological activity.

3. The process of claim 1 wherein the protein is a lymphokine.

4. The process of claim 1 wherein the protein is IFN-β or IL-2.

5. The process of claim 4 wherein the pH is below about 9.

6. The process of claim 4 wherein the pH is between 5.5 and 9.

7. The process of claim 1 wherein the protein is IL-2 and the pH is between 6.5 and 7.5.

8. The process of claim 1 wherein the protein is IFN-β and the pH is between 6.5 and 9.0.

9. The process of claim 1 wherein said concentration of synthetic protein is in the range of about 0.3 to about 0.7 mg/ml.

10. The process of claim 1 wherein the protein is an IL-2, said mol ratio is in the range of about 1:1 and about 5:1, the pH is between 6.5 and 7.5, and the concentration of synthetic IL-2 in the reaction mixture is in the range of about 0.3 to about 0.7 mg/ml.

11. The process of claim 1 wherein the protein is IFN-β, said mol ratio is in the range of about 1:1 and about 5:1, the pH is between 6.5 and 9.0 and the concentration of synthetic IFN-β in the reaction mixture is in the range of about 0.3 to about 0.7 mg/ml.

12. The process of claim 1 wherein after said oxidation the oxidized product is purified using a gel filtration method.

13. The process of claim 12 wherein the filtration is carried out using a G-25 Sephadex desalting column.

14. The preparation of claim 1 wherein the preparation contains less than about 1% by weight oligomers.

15. The preparation of claim 1 wherein the synthetic protein is a synthetic mutein of a biologically active protein which protein has at least one cysteine residue that is free to form a disulfide link and is nonessential to said biological activity, said mutein having at least one of said cysteine residues deleted or replaced by another amino acid.

16. A cystine-containing IL-2 preparation derived from synthetic microbially produced IL-2 having fully reduced cysteines comprising cystine-containing IL-2 which:
   (i) has the same disulfide bridging as native human IL-2;
   (ii) is substantially free of oligomers; and
   (iii) contains less than about 15% by weight of isomers having disulfide bridging different from native human IL-2.

17. A cystine-containing protein preparation derived from a synthetic microbially produced, unglycosylated protein having fully reduced cysteines and having an amino acid sequence substantially identical to a useful protein which sequence includes cysteines which is the useful protein are linked intramolecularly to form a cystine, which preparation consists essentially of a cystine-containing protein which:
   (i) has the same disulfide bridging as the native useful protein;
   (ii) is substantially free of oligomers; and
   (iii) contains less than about 15% by weight of isomers having disulfide bridging different from the native useful protein.

18. The preparation of claim 16 wherein the preparation contains less than about 1% by weight oligomers.

19. A cystine-containing IFN-β preparation derived from synthetic microbially produced, unglycosylated IFN-β having fully reduced cysteines, which preparation consists essentially of cystine-containing IFN-β which:
   (i) has the same disulfide bridging as native human IFN-β;

(ii) is substantially free of oligomers; and (iii) contains less than about 15% by weight of isomers having disulfide bridging different from native human IFN-$\beta$.

20. The preparation of claim 19 wherein the preparation contains less than about 1% by weight oligomers.

21. The preparation of claim 16 wherein said IL-2 is des-ala IL-2$_{ser125}$.

22. The preparation of claim 19 wherein said IFN-$\beta$ is IFN-$\beta_{ser17}$.

* * * * *

UNITED STATES PATENT AND TRADEMARK OFFICE
CERTIFICATE OF CORRECTION

PATENT NO. : 4,530,787
DATED : July 23, 1985
INVENTOR(S) : Ze'ev Shaked and Sidney N. Wolfe It is certified that error appears in the above—identified patent and that said Letters Patent is hereby corrected as shown below:

In column 13, line 31, change "buffer." to read -- buffer, --.

In column 14, line 27, change "1" to read -- 17 --.

In column 14, line 29, change "1" to read -- 17 --.

In column 14, line 50, change "is" to read -- in --.

Signed and Sealed this

Fifteenth Day of October 1985

[SEAL]

Attest:

DONALD J. QUIGG

Attesting Officer

Commissioner of Patents and
Trademarks—Designate

Notice of Adverse Decision in Interference

In Interference No. 101,731, involving Patent No. 4,530,787, Z. Shaked, S. N. Wolfe, CONTROLLED OXIDATION OF MICROBIALLY PRODUCED CYSTEINE-CONTAINING PROTEINS, final judgment adverse to the patentees was rendered Jan. 7, 1992, as to claims 7, 8, 12 and 13.

*(Official Gazette August 25, 1992.)*

REEXAMINATION CERTIFICATE (2064th)
United States Patent [19]
Shaked et al.

[11] B1 4,530,787

[45] Certificate Issued Jul. 20, 1993

[54] CONTROLLED OXIDATION OF MICROBIALLY PRODUCED CYSTEINE-CONTAINING PROTEINS

[75] Inventors: Ze'ev Shaked, Berkeley; Sidney N. Wolfe, Richmond, both of Calif.

[73] Assignee: Cetus Corporation, Emeryville, Calif.

Reexamination Request:
No. 90/001,787, Jun. 12, 1989

Reexamination Certificate for:
Patent No.: 4,530,787
Issued: Jul. 23, 1985
Appl. No.: 661,902
Filed: Oct. 17, 1984

Certificate of Correction issued Oct. 15, 1985.

Related U.S. Application Data

[63] Continuation-in-part of Ser. No. 594,351, Mar. 28, 1984, abandoned.

[51] Int. Cl.[5] .............. C07K 15/00; A61K 37/02; A61K 37/66
[52] U.S. Cl. .................. 530/351; 530/345; 530/363; 530/410; 530/808; 530/820; 530/825; 530/350; 530/395; 530/399; 530/402; 424/85.2; 424/85.4; 424/88; 424/85.1; 424/85.6; 435/69.51; 435/811; 435/69.52; 930/141; 930/142
[58] Field of Search ............ 530/351, 350, 395, 402, 530/399, 825; 424/85.2, 85.6, 85.1; 435/68, 70, 172.2, 172.3, 69.51, 69.52

[56] References Cited

U.S. PATENT DOCUMENTS

| | | | |
|---|---|---|---|
| 4,315,852 | 2/1982 | Liebowitz et al. | 530/351 |
| 4,332,892 | 6/1982 | Ptashne et al. | 435/172.3 |
| 4,390,623 | 6/1983 | Frabricius et al. | 424/85.2 |
| 4,401,756 | 8/1983 | Gillis et al. | 530/351 |
| 4,448,879 | 5/1984 | Fabricius et al. | 435/69.52 |
| 4,464,295 | 8/1984 | Bhaduri et al. | 424/92 |
| 4,464,355 | 8/1984 | Fabricius et al. | 424/85.2 |
| 4,476,049 | 10/1984 | Kung | 424/85.4 |
| 4,490,289 | 12/1984 | Stern | 530/351 |
| 4,508,833 | 4/1985 | Sonneborn et al. | 436/543 |
| 4,511,502 | 4/1985 | Builder et al. | 530/351 |
| 4,511,503 | 4/1985 | Olson et al. | 530/351 |
| 4,512,922 | 4/1985 | Jones et al. | 436/548 |
| 4,518,526 | 5/1985 | Olson | 436/548 |
| 4,518,584 | 5/1985 | Mark et al. | 435/172.3 |
| 4,564,593 | 1/1986 | Tsukamoto et al. | 435/91 |
| 4,569,790 | 2/1986 | Koths et al. | 530/351 |
| 4,588,585 | 5/1986 | Mark et al. | 435/69.58 |
| 4,675,383 | 6/1987 | Bohlen et al. | 530/351 |
| 4,738,927 | 4/1988 | Taniguchi et al. | 435/243 |
| 4,752,798 | 2/1986 | Koths et al. | 530/351 |
| 4,778,879 | 10/1988 | Mertelsmann et al. | 530/351 |
| 4,789,658 | 12/1988 | Yoshimoto et al. | 435/172.3 |
| 4,853,332 | 8/1989 | Mark et al. | 435/69.52 |

FOREIGN PATENT DOCUMENTS

| | | |
|---|---|---|
| 0041313 | 12/1981 | European Pat. Off. |
| 0088195 | 9/1983 | European Pat. Off. |
| 0091539 | 10/1983 | European Pat. Off. |
| 0092163 | 10/1983 | European Pat. Off. |
| 0094317 | 11/1983 | European Pat. Off. |
| 0111344 | 6/1984 | European Pat. Off. |
| 0118617 | 9/1984 | European Pat. Off. |
| 0118977 | 9/1984 | European Pat. Off. |
| 0119621 | 9/1984 | European Pat. Off. |
| 0121352 | 10/1984 | European Pat. Off. |
| 0128467 | 12/1984 | European Pat. Off. |
| 0132359 | 1/1985 | European Pat. Off. |
| 0142268 | 5/1985 | European Pat. Off. |
| 0145390 | 6/1985 | European Pat. Off. |
| 0147819 | 7/1985 | European Pat. Off. |
| 0158198 | 10/1985 | European Pat. Off. |
| 0158487 | 10/1985 | European Pat. Off. |
| 0148098 | 11/1980 | Japan . |

OTHER PUBLICATIONS

Robb et al, Molecular Immunology, 18(12), 1087–94, (1981).

Gillis et al, J. Immunol., 124(4), 1954, (1980).

Guarante et al, Cell, 20, 543–53, 1980.

Devos et al, Nucleic Acids Research, 11(13), Jul. 13, 1983, pp. 4307–4323.

Taniguchi, T. et al, *Nature*, 302:305–310 (Mar. 24, 1985).

Taniguchi, T. et al, *Proc. Natl. Acad. Sci., USA*, 77:5230-5233 (Sep. 1980).
Derynck, R. et al, *Nature*, 285:542-547 (Jun. 19, 1980).
Weir, M. P. et al, *J. Biochem.*, 245:85-91 (1987).
Tsuji, T. et al, *Biochem.*, 26:3129-3134 (1987).
Liu, T.-Y., *The Proteins*, vol. III, pp. 255-263 (Academic Press 1978).
Sato, T. et al, *J. Biochem.*, 101:525-534 (1987).
Wang, A. et al, *Science*, 224:1431-1433 (1984).
Kenny, W. C. et al, *Lymphokine Research*, 5:523:527 (1986).
Arakawa, T. et al, *Biochem.*, 25:8247-8277 (1986).
Mark, D. F. et al, *Proc. Natl. Acad. Sci. USA*, 81:5662-5666 (1984).
Ju, G. et al, *J. Biol. Chem.*, 262:5723-5731 (1987).
Watson et al., *J. Exp. Med.*, 150:849-861 (1979).
Derynck et al, *Nature*, 287:193-197 (1980).
Gillis et al, *J. Immunol.*, 124:1954-1962 (1980).
Mochizuki et al, *J. Immunol. Meth.*, 39:185-201 (1980).
Henricksen et al, *Cell. Immunol.* 73:106-114 (1982).
Ihle et al, *J. Immunol.* 129:2431-2436 (1982).
Welte, K. et al., *J. Exp. Med.*, 156:454-464 (1982).
*Lymphokine Res.*, FASEB Editorial, (I)2, (1982).
Coughlin, R. T. et al, *Fed. Proc.*, 42(7):2022 (1983).
Devos et al, *Nucleic Acid Res.*, 11(13):4307-4323 (1983).
Henderson et al, *J. Immunol.*, 131(2):810-815 (1983).
Milstone et al, *Biochem. Biophys. Res. Comm.*, 115(3):762-768 (1983).
Riendeau et al., *J. Biol. Chem.*, 258(20):12114-12117 (1983).
Robb, R. J. et al, *Immunol. Today*, 5(7):203-209 (1984).
Rosenberg, S. A., et al, *Science* 223:1412-1415 (1984).
Stern, A. S., et al, *Proc. Natl. Acad. Sci.* (USA), 81:871-875 (1984).
"Chromatographic Removal of Pyrogens", *Bio/Technology*, 1035-1038 (1984).
Lahm et al, *J. Chromat.*, 326:357-361 (1985).
Rosenberg et al, *New Eng. J. Med.*, 313:1485-1492 (1985).
Farrar, J. et al, *Immunol. Rev.* 63:129-166 (1982).
Kawamura, H. et al, *J. Exp. Med.*, 162:381-386 (1985).
Mier, J. et al, *J. Immunol*, 128:1122-1127 (1982).
Reed, S. et al, *J. Immunol*, 133:3333-3337 (1984).
Ruscetti, F. et al, *Blood*, 57:379-394 (1981).
Stotter, H. et al, *Eur. J. Immunol.* 10:719-722 (1980).
Caplan et al, *J. Immunol.* 126(4):1351-1354 (1981).
Perraudin et al, *J. Bio. Chem.* 258(19):11834-11839.
Little, C. et al, *Arch. Biochem. Biophys.*, 122:402-410 (1967).
Wetzel et al, *UCLA Symp. Mol. Cell. Biol.*, 25:365-376 (1982).
Rudolph, R. et al, *Hoppe-Seyler's Z. Physiol. Chem. Bd.*, 364:813-820 (1983).
Collins Cobuild English Language Dictionary (1987), p. 1131.
Mitraki, A. et al, *Bio/Technology*, 7:690-696 (1989).
Lehninger, A. L. *Biochemistry*, (Worth Publishers, Inc. 1970), p. 81.
Shephard, H. M. et al, *Nature*, 294:563-565 (1981).
Dickerson, R. E. et al, *The Structure and Action of Proteins*, (W. A. Benjamin, Inc. 1969), p. 86.
Liang, S.-M. et al, *J. Biol. Chem.*, 261:334-337 (1986).

*Primary Examiner*—Garnette D. Draper

[57] ABSTRACT

Method of oxidizing reduced cysteine-containing microbially produced synthetic proteins, such as synthetic IFM-$\beta$ or synthetic IL-2, in a controlled manner so that the synthetic proteins have the same disulfide bridging as their native counterparts. The oxidation employs o-iodosobenzoate as oxidizing agent and is carried out in an aqueous medium at a pH at least about one-half pH unit less than the $pK_a$ of the cysteines to be oxidized, a synthetic protein concentration of less than about 5 mg/ml, and an oxidizing agent:protein mol ratio that is at least stoichiometric, provided that the oxidizing agent is in excess in the terminal portion of the reaction.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–13 is confirmed.

Claims 14–18 and 20 are cancelled.

Claims 19, 21 and 22 are determined to be patentable as amended.

19. A cystine-containing *unglycosylated* IFN-β preparation *wherein said IFM-β mutein has at least one cysteine residue that is free to form a disulfide link and is nonessential to said biological activity, said mutein having at least one of said cysteine residues deleted or replaced by another amino acid and wherein said IFN-β mutein is derived from synthetic microbially produced, unglycosylated IFN-β mutein having fully reduced cysteines, which preparation consists essentially of cystine-containing IFN-β mutein, which:*
  (i) *has the same disulfide bridging as native human IFN-β with no or minimal overoxidation products; and*
  (ii) [is substantially free] *contains greater than 0%, but less than about 1%, by weight of detectable* oligomers[; *and*
  (iii) *contains less than about 15% by weight of isomers having disulfide bridging different from native human IFN-β*].

21. [The] *A cystine-containing unglycosylated IL-2* preparation . [of claim 16] *derived from synthetic microbially produced unglycosylated IL-2 having fully reduced cysteines comprising cystine-containing IL-2 which:*
  (i) *has the same disulfide bridging as native human IL-2 with no or minimal overoxidation products;*
  (ii) *contains greater than 0%, but less than about 1%, by weight of detectable oligomers; and*
  (iii) *contains less than about 15% by weight of isomers having disulfide bridging different from native human IL-2,* wherein said IL-2 is des-ala IL-2$_{ser125}$.

22. The preparation of claim 19 wherein said IFN-β mutein is IFN-β$_{ser17}$.

* * * * *